United States Patent [19]

Horodniceanu et al.

[11] Patent Number: 4,537,790

[45] Date of Patent: * Aug. 27, 1985

[54] PROCESS FOR GROWING CELL CULTURES OF DIPLOID CELLS ON CELL SUPPORTS

[75] Inventors: Florian Horodniceanu, Meudon; Raphaël Le Fur, Louviers, both of France

[73] Assignee: Institut Pasteur, Paris, France

[ * ] Notice: The portion of the term of this patent subsequent to Mar. 12, 2002 has been disclaimed.

[21] Appl. No.: 493,715

[22] Filed: May 11, 1983

Related U.S. Application Data

[60] Division of Ser. No. 93,050, Nov. 13, 1979, Pat. No. 4,504,547, which is a continuation of Ser. No. 930,226, Aug. 2, 1978, abandoned.

[30] Foreign Application Priority Data

Aug. 8, 1977 [FR] France .................................. 77 24421

[51] Int. Cl.³ .......................... A01N 1/02; C12N 11/08
[52] U.S. Cl. ........................................ 427/2; 427/221; 427/222; 427/314; 427/316; 427/385.5; 427/389.7; 435/180; 435/240; 435/241; 435/284; 435/285; 435/286; 435/948
[58] Field of Search ............... 435/180, 240, 241, 284, 435/285, 286, 948; 427/2, 316, 314, 315, 212, 215, 322, 221, 299, 385.5, 389.7, 222; 422/26

[56] References Cited

U.S. PATENT DOCUMENTS

| | | | |
|---|---|---|---|
| 3,097,070 | 7/1963 | Aldrich et al. | 422/102 |
| 3,102,082 | 8/1963 | Brewer | 435/30 |
| 3,282,722 | 11/1966 | Hailstone | 428/441 |
| 3,437,553 | 4/1969 | Hailstone | 428/441 |
| 3,532,605 | 10/1970 | Riera | 215/1 R |
| 3,746,196 | 7/1973 | Sako et al. | 215/1 C |
| 3,767,790 | 10/1973 | Guttag | 435/243 |
| 3,860,490 | 1/1975 | Guttag | 435/243 |
| 3,910,819 | 10/1975 | Rembaum et al. | 435/284 |
| 4,036,693 | 7/1977 | Levine et al. | 435/284 |

*Primary Examiner*—S. L. Childs
*Attorney, Agent, or Firm*—Hammond & Littell, Weissenberger & Dippert

[57] ABSTRACT

The present invention relates to a process for growing cell cultures of diploid cells. The process comprises the steps of (a) introducing cell culture medium into a container containing cell support prepared by applying to glass or polysaccharide base support a solution of thermosetting plastic material comprising the reaction product of an aldehyde with a polyvinyl alcohol and then subjecting said support thus-coated to the effect of heat under sufficient conditions to permit hardening of said thermosetting plastic material and the sterilization of the thus-coated support;

(b) adding human or animal diploid cells to the culture medium of step (a) to form a cell-containing culture medium; and (c) maintaining the cell-containing culture medium of step (b) under cell growth conditions.

10 Claims, No Drawings

PROCESS FOR GROWING CELL CULTURES OF DIPLOID CELLS ON CELL SUPPORTS

CROSS-REFERENCE TO RELATED APPLICATIONS

This application is a divisional of co-pending U.S. patent application Ser. No. 93,050, filed Nov. 13, 1979, now U.S. Pat. No. 4,504,547, which in turn is a continuation of U.S. patent application Ser. No. 930,226, filed Aug. 2, 1978, now abandoned.

BACKGROUND OF THE INVENTION

1. Field of the Invention

The present invention relates to the field of cell cultures and more particularly to the use of thermosetting plastics materials for improving supports used for cell growth.

2. Description of the Prior Art

It is known that cell cultures are generally produced either in monolayers on supports in the presence of liquid nutrient media, or in suspension in liquid nutrient medium, or in the presence of a semi-solid nutrient medium (agarose).

Suitable supports for cell growth are particularly neutral glass or plastics, generally based on polystyrene, which have undergone special treatment to render them suitable for cell growth. These plastics are for a single use and are sterilized by a physical treatment with the exclusion of heat. Recently, the use has commenced, for cell cultures of microsupports based on glass, polysaccharides ("Sephadex") or of plastics materials.

The supports for cell cultures must be of such a nature that the cells adhere easily thereto; they must not be toxic for the cells nor inhibit their growth. In addition, they must permit microscopic observations to be carried out easily.

As regards microsupports, tests have been carried out with glass beads or polystyrene beads; however these microsupports are not satisfactory for obtaining cultures on an industrial scale or are only satisfactory under certain conditions.

In this connection, reference may be made to the article of A. L. Van Wezel entitled "Microcarrier Cultures of Animal Cells" in the treatise "Tissue Culture Methods and Application" edited by Paul F. KRUSE JR and M. K. PATTERSON JR Academic Press New York and London 1973. It is, for example, indicated that cells do not adhere in a sufficiently fast manner to plastics beads, such as polystyrene beads or beads of "Rilsan", trademark for a polyamide also known as nylon 11, which beads have undergone special treatment. On the other hand, it is pointed out that tests have been carried out with "Spherosil" beads, "Spherosil" being the tradename for microbeads made of silica these beads do not seem suitable for industrial cultures considering the relatively high density of these beads in the culture media. It is noted also that the various types of ion exchange resins comprised of dextran chains cross-linked to form a tridimensional matrice of polysaccharide and having diethylamino functional groups, known under the commercial name "DEAE-Sephadex" and available from PHARMACIA FINE CHEMICALS AB, UPPSALA, SWEDEN, do not all have the same properties as supports for cell cultures.

To improve the properties of "DEAE-Sephadex A 50" beads, it has already been proposed to coat them with nitrocellulose (see the article of A. L. Van Wezel mentioned above).

GENERAL DESCRIPTION OF THE INVENTION

A means has now been found for treating supports for cell cultures, which permits their use under various operational conditions and notably their use for seeding, growth and trypsination of cell cultures, in particular of human or animal diploid cell cultures, said means according to the invention consisting of applying on base supports a thermosetting plastics material under the conditions indicated below in detail.

Thus, the present invention relates to a process for producing supports for cell cultures which consists of applying to base supports a solution of a thermosetting plastics material and of then subjecting said supports thus-coated to the effects of heat under conditions sufficient to permit the hardening of said thermosetting plastics and the sterilization of said thus-coated supports.

The present invention also relates to supports for cell cultures constituted by a base support bearing a thermo-hardened coating.

In the present description, the expression "base supports" or "basic supports" means any currently used support within the field concerned which are based on glass or polysaccharides; these supports can have a flat surface or a spherical surface.

By way of examples of such supports, may be mentioned Petri dishes, Roux dishes, beads, notably beads constituted from products known under the tradename "DEAE-Sephadex" and any other glass bottle or material used for cell cultures.

Thermosetting plastics which are suitable for the purposes of the invention must not be toxic to the cells; they must, preferably, be transparent to permit microscopic observations; moreover, they must be such that the cells adhere easily and firmly to said coated supports. As regards the application to microsupports, these plastics must form a film around each microsupport without forming an aggregate. In addition, these plastics must resist the final autoclaving in liquid phase (sterilization).

Among the thermosetting plastics which are suitable for the purposes of the present invention, may be mentioned notably the reaction products of an aldehyde with a polyvinyl alcohol, for example the reaction product of formaldehyde or of butyraldehyde with a polyvinyl alcohol.

By way of preferred thermosetting plastics according to the invention, may be mentioned the products known under the tradenames "RHOVINAL B" and RHOVINAL F" sold by the Societe RHONE POULENC Polymeres.

The products known by the tradename "RHOVINAL B" are polyvinyl butyral polymers which result from the reaction of butyraldehyde with polyvinyl alcohol; among these products, are particularly preferred "RHOVINAL B 10/20".

In the above-mentioned names, the first figure indicates the viscosity in millipoises of a 5% solution of said product in 95° ethyl alcohol at 20° C. and the second figure indicates the percentage by weight of polyvinyl alcohol groups in the molecule.

The products known under the tradename "RHOVINAL F" are polyvinyl formals which result from the reaction of formal with polyvinyl alcohol.

The thermosetting plastics are applied in the process of the invention in the form of solutions in suitable solvents. The solvents which are suitable are the solvents for said plastics which are preferably volatile. The use of non-volatile solvents necessitates intensive washings to remove any trace of solvents which would be toxic to the cultures. Preferably, chloroform, methanol or a mixture of chloroform and methanol are used.

The solutions of thermosetting plastics applied according to the process of the invention contain a sufficient amount of thermosetting plastics material to obtain under operational conditions a continuous film permitting optimal cell culture, that is to say cell multiplication for at least a week. It will be for the specialist to determine the concentration of the solution to be used.

By way of example, it may be indicated that when the thermosetting plastic is "RHOVINAL B 10/20", 0.5 to 2% solutions, preferably 1%, of RHOVINAL B 10/20 are suitable, said percentages being counted in weight.

The microsupports treated according to the process of the invention are preferably washed before the application of the thermosetting plastics solution, by means for example of an isotonic buffer, such as a pH 7.2 phosphate buffer, and passed into the autoclave.

The supports treated with the thermosetting plastics solution are then heat treated, in an oven or an autoclave, at a sufficient temperature to permit the hardening of said thermosetting plastics and the sterilization of the said thus-coated support. Generally, one operates at a temperature comprised between about 120° C. (autoclave) and 180° C. (oven).

When the supports are in spherical form, for example in the form of fine particles of a size ranging from 100 to 200 μm (after swelling), it is advantageous to maintain the gel constituted from fine particles in suspension in the thermosetting plastics solution at a temperature of about 37° C. for a sufficient time, for example for 24 to 48 hours, for the thermosetting plastics material to adhere over their whole surface of the fine particles.

After the heat treatment in an autoclave, the supports, particularly the "Sephadex" microsupports, must be washed in an isotonic buffer to remove the traces of solvent, then sterilized and preserved until their use.

In a modification of the operation of the process of the invention, it is advantageous to wash the supports (beads and microsupports) after the heat treatment with an isotonic buffer containing Ca++ or Mg++ ions and to pass them to the autoclave; this treatment improves the adherence of the cells to the microsupports.

In the present description, the expression "pass into an autoclave" signifies that the supports are treated in an autoclave at a temperature of about 120° C. for a sufficient time for sterilization.

Before their use, it is advantageous to rinse the microsupports in a culture medium containing about 10% of veal serum.

The preferred supports according to the present invention are the supports for cell cultures, constituted by a basic support, such as glass or polysaccharides, of flat or spherical shape, for example Petri dishes, Roux dishes, i.e., bottles or flasks for the culture of bacteria and cells having a volume of from 30 ml to 5 l and having two parallel plane surfaces, or beads bearing a thermoset coating constituted by a polymer resulting from the product of the reaction of an aldehyde and of a polyvinyl alcohol, such as a polyvinyl butyral or polyvinyl formal polymer.

The supports according to the invention can be used for the cultivation of human or animal diploid cells or any other cell (primary explant, continuous line) adapted for cultivation in monolayers. In addition, these supports may be used for any conventional operations of seeding and of trypsination of cell cultures.

The cells which multiply an microsupports according to the invention may be used as a substrate for virus production. The virus harvesting is carried out by a taking up of the medium after decantation of the beads. This virus can then be purified for the preparation of vaccines and of viral antigenes. The cell cultures obtained by this process may also serve for the production of interferon, of enzymes or of hormones, or of any other substances of cellular origin.

DESCRIPTION OF PREFERRED EMBODIMENTS

The present invention will now be illustrated in more detail by the following non-limiting examples.

EXAMPLE 1

Treatment of a flat surface: Roux dish

RHOVINAL B10/20 was dissolved in chloroform to a concentration of 0.5 to 1%. The "RHOVINAL" was poured into a cell culture dish so as to fill the dish. The contents were poured into a second dish, and then successively into all the dishes. The dishes were allowed to drain for five minutes on the flask stand and then they were sterilized in the oven for one hour at 180° C. During the sterilization, the film of "Rhovinal" solution which adhered to the surface of the dish was hardened by the heat.

EXAMPLE 2

Treatment of a Spherical Surface

Beads constituted by the product known under the tradename "DEAE-Sephadex A-50" were used; these beads had a diameter of 80 to 100 μm.

10 g of "DEAE-Sephadex A-50" beads were washed several times by means of a pH 7.2 isotonic phosphate buffer and passed in an autoclave. The beads were suspended in 600 ml of chloroform solution of "Rhovinal B 10/20" (1 l of chloroform contained 15 g of Rhovinal). The suspension thus obtained was left for one hour at 37° C. The excess chloroform solution (lower phase) was removed, preserving the DEAE-Sephadex gel (upper phase). The gel was placed for 24 hours at 37° C. and then for one hour in the autoclave (120° C.). The beads were then washed several times during 24 hours in a pH=7.2 isotonic phosphate buffer, then passed into the autoclave in the presence of a phosphate buffer containing Ca++ and Mg++ ions.

The thus treated beads can be preserved in sterile condition until their use; it is then recommended to rinse them once in a culture medium containing 10% of veal serum.

EXAMPLE 3

Treatment of a Spherical Surface

Beads constituted by the product known under the tradename "DEAE-Sephadex A-50" were again used.

After washing with an isotonic phosphate buffer, 10 g of "DEAE-Sephadex A-50" were rinsed in 600 ml of methanol. After 24 hours at 37° C., the excess of methanol above the gel was removed and the beads were suspended in 600 ml of 0.5% "Rhovinal B 10/20" solution; the solvent used was constituted by a mixture of chloroform (75%) and methanol (25%). After 48 hours at 37° C., the excess of "Rhovinal" solution was removed and the gel was treated for one hour in the autoclave (120° C.). The beads were then washed and rinsed by the operational method described in Example 2.

EXAMPLE 4

Use of Roux dishes treated by the operational method described in Example 1.

In a Roux dish, treated according to Example 1, 100 ml of culture medium was introduced (Eagle base medium or Eagle minimum medium) containing about 10% of veal serum; it was seeded with 50,000 human diploid cells per ml of culture medium. At the end of 24 hours, the cells had adhered 100% to the support according to the invention. Then the culture was continued for 7 to 8 days so as to obtain a minimal final concentration of 200,000 cells per cm$^2$ of support.

EXAMPLE 5

Use of DEAE-Sephadex beads treated by the operational method described in Example 2.

Into a flask with stirring, were introduced the culture medium (Eagle base medium or Eagle minimum medium) containing about 10% of veal serum and 1 to 2 mg/ml of "DEAE-Sephadex A-50" treated with "Rhovinal" as in Example 2. It was seeded with $10^5$ human diploid cells per ml of culture medium (MRC 5 cell line).

For 24 hours at 37° C. the cells were slowly stirred (60 rpm) and had adhered 100% to the beads; then the cell culture was continued for 7 to 8 days (90 rpm) so as to obtain a final cell concentration of $10^6$ cells/ml. During the 7 to 8 days of cultivation, it was necessary to keep the pH at a constant value: 7.2–7.4.

By way of comparison, a cultivation of diploid cells under the same conditions as above but using "DEAE-Sephadex A-50" beads which had not been treated in accordance with the process of the invention, was carried out. After 7 to 8 days of cultivation, the final cell concentration was only $10^5$ cells per ml.

We claim:

1. A process for growing cell cultures of human or animal diploid cells which comprises the steps of
   (a) introducing cell culture medium into a container containing cell support prepared by applying to glass or polysaccharide base support a solution of a thermosetting plastic material comprising the reaction product of an aldehyde with a polyvinyl alcohol and then subjecting said support thus-coated to the effect of heat under sufficient conditions to permit hardening of said thermosetting plastic material and the sterilization of the thus-coated support;
   (b) adding human or animal diploid cells to the culture medium of step (a) to form a cell-containing culture medium; and
   (c) maintaining the cell-containing culture medium of step (b) under cell growth conditions.

2. The process of claim 1, wherein the thermosetting plastic material is a polyvinyl butyral polymer resulting from the reaction of butyraldehyde with a polyvinyl alcohol whose viscosity at 20° C. of a 5% solution in 95° ethyl alcohol is 10 millipoises and whose percentage by weight of polyvinyl alcohol groups is 20.

3. The process of claim 1, wherein the base support is a Petri dish, a Roux dish, or "DEAE-Sephadex" beads.

4. The process of claim 1, wherein the base support coated with the thermosetting plastic solution is subjected to the effect of heat at a temperature of from 120° to 180° C.

5. The process of claim 1, wherein, before the application of the thermosetting plastic solution, the base support is washed by means of an isotonic buffer and then passed into an autoclave.

6. The process of claim 1, wherein the base support comprises beads or microsupports and wherein, prior to introduction of cell culture medium in step (a), the base support is heat treated in an autoclave, rinsed with an isotonic buffer containing Ca$^{++}$ and Mg$^{++}$ ions, and passed into the autoclave for sterilization.

7. The process of claim 1, wherein the base support has a flat shape or comprises spherical shapes.

8. The process of claim 1, wherein the thermosetting plastic material is a polyvinyl butyral or polyvinyl formal polymer.

9. The process of claim 8, wherein the thermosetting plastic material is a polyvinyl butyral polymer resulting from the reaction of butyraldehyde with a polyvinyl alcohol whose viscosity at 20° C. of a 5% solution in 95° ethyl alcohol is 10 millipoises and whose percentage by weight of polyvinyl alcohol groups is 20.

10. In a process for growing human or animal diploid cells in a culture medium,
    the improvement which comprises growing said cells in contact with cell support prepared by applying to glass or polysaccharide base support a solution of a thermosetting plastic material comprising the reaction product of an aldehyde with a polyvinyl alcohol and then subjecting said support thus-coated to the effect of heat under sufficient conditions to permit hardening of said thermosetting plastic material and the sterilization of the thus-coated support.

* * * * *